(12) United States Patent
Bogue et al.

(10) Patent No.: US 8,282,954 B2
(45) Date of Patent: Oct. 9, 2012

(54) METHOD FOR MANUFACTURING EDIBLE FILM

(75) Inventors: Beuford A. Bogue, New Carlisle, IN (US); Garry L. Myers, Kingsport, TN (US)

(73) Assignee: MonoSol Rx, LLC, Warren, NJ (US)

( * ) Notice: Subject to any disclaimer, the term of this patent is extended or adjusted under 35 U.S.C. 154(b) by 622 days.

(21) Appl. No.: 12/334,906

(22) Filed: Dec. 15, 2008

(65) Prior Publication Data

US 2010/0150987 A1    Jun. 17, 2010

(51) Int. Cl.
  *A61F 13/00*   (2006.01)
  *A61K 47/00*   (2006.01)

(52) U.S. Cl. ........................ 424/433; 424/439

(58) Field of Classification Search .................. 424/433, 424/439
  See application file for complete search history.

(56) References Cited

U.S. PATENT DOCUMENTS

| | | |
|---|---|---|
| 3,007,848 A | 11/1961 | Stroop |
| RE33,093 E | 10/1989 | Schiraldi et al. |
| 5,118,508 A | 6/1992 | Kikuchi et al. |
| 5,605,696 A | 2/1997 | Eury et al. |
| 5,629,003 A | 5/1997 | Horstmann et al. |
| 5,766,620 A | 6/1998 | Heiber et al. |
| 5,800,832 A | 9/1998 | Tapolsky et al. |
| 5,806,284 A | 9/1998 | Gifford |
| 5,891,461 A | 4/1999 | Jona et al. |
| 6,072,100 A | 6/2000 | Mooney et al. |
| 6,103,266 A | 8/2000 | Tapolsky et al. |
| 6,284,264 B1 | 9/2001 | Zerbe et al. |
| 6,375,963 B1 | 4/2002 | Repka et al. |
| 6,667,060 B1 | 12/2003 | Vandecruys et al. |
| 6,800,329 B2 | 10/2004 | Horstmann et al. |
| 6,824,829 B2 | 11/2004 | Berry et al. |
| 7,005,142 B2 | 2/2006 | Leon |
| 7,425,292 B2 | 9/2008 | Yang et al. |
| 7,579,019 B2 | 8/2009 | Tapolsky et al. |
| 2003/0107149 A1 * | 6/2003 | Yang et al. ................ 264/134 |
| 2003/0124176 A1 | 7/2003 | Hsu et al. |
| 2004/0096569 A1 | 5/2004 | Barkalow et al. |
| 2004/0191302 A1 | 9/2004 | Davidson |
| 2005/0048102 A1 | 3/2005 | Tapolsky et al. |
| 2005/0118217 A1 | 6/2005 | Barnhart et al. |
| 2005/0232977 A1 | 10/2005 | Khan |
| 2006/0210610 A1 | 9/2006 | Davidson et al. |
| 2007/0087036 A1 | 4/2007 | Durschlag et al. |
| 2007/0148097 A1 | 6/2007 | Finn et al. |

FOREIGN PATENT DOCUMENTS

| | | |
|---|---|---|
| EP | 0598606 B1 | 6/1999 |
| EP | 1591106 A1 | 2/2005 |
| WO | 03030882 A1 | 4/2003 |
| WO | 2008011194 A2 | 1/2008 |

OTHER PUBLICATIONS

European Search Report cited in EPO Application No. 09179080.8 (Mar. 11, 2010).
Lazaridou et al., "Thermophysical proprties of chitosan, chitosan-starch and chitosan-pullulan films near the glass transition," Carbohydrate Polymers 48: 179-190 (2002).
Repka et al., "Bioadhesive Properties of hydroxypropylcellulose topical films produced by hot melt extrusion," Journal of Controlled Release, 70: 341-351 (2001).
Repka et al., "Influence of Vitamin E TPGS on the properties of hydrophilic films produced by hot melt extrusion", International Journal of Pharmaceutics 202: 63-70 (2000).

* cited by examiner

*Primary Examiner* — Ileana Popa
*Assistant Examiner* — Genevieve S Alley
(74) *Attorney, Agent, or Firm* — Hoffmann & Baron, LLP (57) ABSTRACT

The present invention provides a process for making an edible film having a substantially uniform distribution of components, which includes the steps of combining a water-based film polymer solution and a slurry-type mixture comprising a water-active component and a solvent; mixing the polymer solution and slurry-type mixture for about 10 minutes or less; dispensing the mixed solution and slurry-type mixture to form a film; and drying the film to evaporate the water and solvent. Films made by the process are also provided.

34 Claims, 1 Drawing Sheet

METHOD FOR MANUFACTURING EDIBLE FILM

FIELD OF THE INVENTION

The invention relates to rapidly dissolving films and methods of their preparation. The films may also contain a pharmaceutically active component that is uniformly distributed throughout the film. The method incorporates a system to combine and dispense the film-forming composition rapidly, so that the pharmaceutically active component has only limited contact with the water-based solvent. The present invention reduces or eliminates the tendency of the pharmaceutically active component to change its structure, such as by crystallizing, becoming amorphous, dissolving, hydrolyzing, swelling and/or disintegrating.

BACKGROUND OF THE RELATED TECHNOLOGY

Active components, such as drugs or pharmaceuticals, may be prepared in a tablet form to allow for accurate and consistent dosing. However, this form of preparing and dispensing medications has many disadvantages including that a large proportion of adjuvants that must be added to obtain a size able to be handled, that a larger medication form requires additional storage space, and that dispensing includes counting the tablets which has a tendency for inaccuracy. In addition, many persons, estimated to be as much as 28% of the population, have difficulty swallowing tablets. While tablets may be broken into smaller pieces or even crushed as a means of overcoming swallowing difficulties, this is not a suitable solution for many tablet or pill forms. For example, crushing or destroying the tablet or pill form to facilitate ingestion, alone or in admixture with food, may also destroy the controlled release properties.

As an alternative to tablets and pills, films may be used to carry active components such as drugs, pharmaceuticals, and the like. However, historically films and the process of making drug delivery systems therefrom have suffered from a number of unfavorable characteristics that have not allowed them to be used in practice.

Films that incorporate a pharmaceutically active component are disclosed in expired U.S. Pat. No. 4,136,145 to Fuchs, et al. ("Fuchs"). These films may be formed into a sheet, dried and then cut into individual doses. The Fuchs disclosure alleges the fabrication of a uniform film, which includes the combination of water-soluble polymers, surfactants, flavors, sweeteners, plasticizers and drugs. These allegedly flexible films are disclosed as being useful for oral, topical or enteral use. Examples of specific uses disclosed by Fuchs include application of the films to mucosal membrane areas of the body, including the mouth, rectal, vaginal, nasal and ear areas. Examination of films made in accordance with the process disclosed in Fuchs, however, reveals that such films suffer from the aggregation or conglomeration of particles, i.e., self-aggregation, making them inherently non-uniform.

Certain methods of manufacturing film products involve mixing all of the components together, and then dispensing or extruding the mixture into a film. However, when the pharmaceutically active component or other components that react with water-based solvents come into contact with the water-based film solution, they may react in undesirable ways, such as by crystallizing or becoming amorphous. This is especially true when water-active components are in contact with the water-based solution for an extended period of time. When the components crystallize or clump together, the resulting mixture becomes less uniform, as higher dosages of the grouped together components settle in various areas of the mixture, and also becomes more difficult to prepare films.

When large dosages are involved, even a small change in the dimensions of the film may lead to a large difference in the amount of active present per film. If a sheet of film (also known as a "web") includes areas with lower dosages of active, it is possible that portions of the film may be substantially devoid of any active. Since sheets of film are usually cut into unit doses, certain doses, particularly those falling in the middle of the sheet, may therefore be devoid of or contain an insufficient amount of active for the recommended treatment. Failure to achieve a high degree of accuracy with respect to the amount of active component in the cut film can be harmful to the patient. For this reason, dosage forms formed by processes such as Fuchs may not meet the stringent standards of governmental or regulatory agencies, such as the U.S. Federal Drug Administration ("FDA"), relating to the variation of active in dosage forms. Currently, as required by various world regulatory authorities, dosage forms may not vary more than 10% in the amount of active present. When applied to dosage units based on films, this virtually mandates that uniformity in the film be present.

The benefits of preparing a film that is substantially uniform in composition, without adding additional components are numerous. In addition to the obvious cost-savings through using minimal materials, there is a greater percentage of films that are pharmaceutically acceptable. Thus, less film will be deemed "unacceptable", resulting in less wasted active component. Further, with a more uniform distribution of active, there can be provided a lesser amount of active provided to the mixture overall. When there is a non-uniform distribution of active, more active must be added to the mixture to compensate for those portions that are non-uniform.

Systems for mixing and dispensing urethanes, epoxies, silicones and the like for sealing, potting, and bonding are known. These systems provide a means for rapidly forcing a chemical reaction by mixing, followed by dispensing of the material as the reaction proceeds. In these cases, if the reacted mixture stays in the mixing compartment too long, it will harden, making dispensing difficult, if not impossible. However, until now, these systems have not been used for quickly mixing and dispensing for the purpose of avoiding a chemical reaction.

Therefore, there is a need for methods of manufacture and compositions of film products, which use a minimal number of materials or components, and which allow the various components to mix and dispense rapidly and dry, reducing the amount of time that the water-active components are in contact with the water-based solution.

SUMMARY OF THE INVENTION

In one embodiment there is provided a process for making an edible film having a substantially uniform distribution of components, which includes the steps of: continuously metering a water-based film polymer solution and a mixture of a water-active component and a solvent into an inline mixer, the residence time of the polymer solution and mixture in the mixer being about 1 second to about 5 minutes or less; continuously dispensing the mixed solution and mixture to form a film; and drying the film to evaporate the solvent.

In another embodiment there is provided a method for reducing the interaction between a water-active component and water-based film polymer solution during formation of an edible film, which includes the steps of: continuously metering a water-based film polymer solution and a mixture of a water-active component and a solvent, into an inline mixer, the residence time of the polymer solution and mixture being from about 1 second to about 5 minutes or less; continuously dispensing the mixed solution and mixture to form a film; and drying the film to evaporate the solvent.

In yet another embodiment, there is provided a method of substantially limiting interaction of a pharmaceutical agent with a water-based solvent during the formation of an edible film, which includes the steps of: simultaneously and continuously metering a water-based film polymer solution and a mixture into an inline mixer, wherein the mixture includes a pharmaceutical agent and a solvent, the residence time of the polymer solution and mixture being from about 1 second to about 5 minutes or less; continuously dispensing the mixed solution and mixture to form a film; and drying the film to evaporate the solvent.

DETAILED DESCRIPTION OF THE INVENTION

For the purposes of the present invention the term "non-self-aggregating uniform heterogeneity" refers to the ability of the films of the present invention, which are formed from one or more components in addition to a polar solvent, to provide a substantially reduced occurrence of, i.e., little or no, aggregation or conglomeration of components within the film as is normally experienced when films are formed by conventional methods such as the use of non-uniform particles and a single stream feeding manifold. The term heterogeneity, as used in the present invention, includes films that will incorporate a single component, such as a polymer, as well as combinations of components, such as a polymer and an active agent. Uniform heterogeneity includes the substantial absence of aggregates or conglomerates as is common in conventional mixing and heat drying methods used to form films. Preferably the films of the present invention have a uniform distribution of particles, a uniform height, weight, and density. The term "water-active component" means a component that reacts in the presence of water. In some embodiments, a "water-active component" may refer to a component that may crystallize in the presence of water; in other embodiments it may refer to a component that may become amorphous in the presence of water. In other embodiments, the water-active component may refer to a component that may change its structure in the presence of water, such as by dissolving, hydrolyzing, swelling, and/or disintegrating.

Also, as used herein, the term "uniformity" means that the content per unit volume of substance is substantially the same throughout the substance. A uniform film, for example, means that the content per unit volume of film is substantially the same throughout the film.

Furthermore, the films of the present invention may incorporate a specific drying method to provide for a more substantially uniform thickness and uniformity of content, which is not provided by the use of conventional drying methods used in water-based polymer systems. The absence of a uniform thickness detrimentally affects uniformity of component distribution throughout the area of a given film.

The film products of the present invention are produced by a combination of a properly selected polymer and a polar solvent, optionally including an active component as well as other fillers known in the art. In some embodiments, a non-volatile solvent or low-volatility solvent may be used. These films provide a non-self-aggregating uniform heterogeneity of the components within them by utilizing a selected casting, deposition or extrusion method, and a controlled drying process. Examples of controlled drying processes include, but are not limited to, the use of the apparatus disclosed in U.S. Pat. No. 4,631,837 to Magoon ("Magoon"), herein incorporated by reference, as well as other drying methods as set forth in the present applicants' U.S. Pat. Nos. 7,425,292 and 7,357,891, which are additionally incorporated herein by reference in their entirety.

The products and processes of the present invention rely on the interaction among various steps of the production of the films in order to provide films that substantially reduce the self-aggregation of the components within the films. Specifically, the reduction in the time that the water-active components are in contact with the water-based materials in the film-forming suspension helps maintain uniformity and controlled processing. Using a system that adds in separate components, mixes them, and dispenses the mixture very rapidly allows for a more uniform film composition.

Desirably, there is a high level of uniformity in the films prepared by the present invention. Specifically, there is desirably less than about a 10% change in the particle content per unit volume throughout the film composition. More desirably, there is less than 5% change, and most preferably there is less than 1% change in the particle content per unit volume throughout the film composition.

Other film-forming methods may be used in conjunction with the methods of the present invention, including the use of a doctor roll, which is a device which marginally or softly touches the surface of the film and controllably disposes the particles onto the film surface, to level the mixed suspension in the system. While the use of a doctor roll is optional, the preferred method is to use a doctor roll in the "on" position while manufacturing the film.

Moreover, the films of the present invention may contain particles that are sensitive to temperature, such as flavors, which may be volatile, or drugs, which may have a low degradation temperature. In such cases, the drying temperature may be decreased while increasing the drying time to adequately dry the uniform films of the present invention. Furthermore, bottom drying also tends to result in a lower internal film temperature as compared to top drying. In bottom drying, the evaporating vapors more readily carry heat away from the film as compared to top drying which lowers the internal film temperature. Such lower internal film temperatures often result in decreased drug degradation and decreased loss of certain volatiles, such as flavors.

Furthermore, particles or particulates may be added to the film-forming composition or matrix after the composition or matrix is cast into a film. For example, particles may be added to the film prior to the drying of the film. Particles may be controllably added to the film and disposed onto the film through any suitable techniques. Such suitable techniques include the use of a doctor roll as described above, the use of an additional roller to place the particles on the film surface, spraying the particles onto the film surface, and the like. The particles may be placed on either or both of the opposed film surfaces, i.e., the top and/or bottom film surfaces. Desirably, the particles are securably disposed onto the film, such as being embedded into the film. Moreover, such particles are desirably not fully encased or fully embedded into the film, but remain exposed to the surface of the film, such as in the case where the particles are partially embedded or partially encased.

The particles may be any useful organoleptic agent, cosmetic agent, pharmaceutical agent, or combinations thereof. Desirably, the pharmaceutical agent is a taste-masked or a controlled-release pharmaceutical agent. Useful organoleptic agents include flavors and sweeteners. Useful cosmetic agents include breath freshening or decongestant agents, such as menthol, including menthol crystals.

Monitoring and control of the thickness of the film also contributes to the production of a uniform film by providing a film of uniform thickness. The thickness of the film may be monitored with gauges such as Beta Gauges. A gauge may be coupled to another gauge at the end of the drying apparatus, i.e. drying oven or tunnel, to communicate through feedback loops to control and adjust the opening in the coating apparatus, resulting in control of uniform film thickness.

The film products are generally formed by combining a properly selected polymer and polar solvent, as well as any active component or filler as desired to create a film polymer solution. The solution may be an aqueous solution of the solvent and polymer. The particles are sieved to achieve substantial particle size uniformity prior to formation. Desirably, the solvent content of the combination is at least about 30% by weight of the total combination of components. The material is then formed into a film, desirably by roll coating, and then dried, desirably by a rapid and controlled drying process to maintain the uniformity of content per unit volume of the film, more specifically, a non-self-aggregating uniform heterogeneity. The resulting dried film will desirably contain less than about 10% by weight solvent, more desirably less than about 8% by weight solvent, even more desirably less than about 6% by weight solvent and most desirably less than about 2%. The solvent may be water, a polar organic solvent including, but not limited to, ethanol, isopropanol, acetone, methylene chloride, or any combination thereof.

The ratio of the solid particles to the liquid materials should be kept high enough to assist in maintaining uniformity of content per unit volume in the film. If the ratio of solid to liquid materials is too low, uniformity may be affected. In situations where the solid portion (% solids) is too small as compared to the liquid portion (% liquid), there is more space in the solution for the solid particles to move freely, and may result in a slurry with a lack of uniformity of content per unit volume. In contrast, when the ratio of solid particles to liquid materials is sufficiently high, the particles have less space to move freely about, and the slurry tends to self-regulate with respect to the uniformity of content per unit volume. With other dosage forms, such as tablets and capsules, the volumetric ratio of the piece is set. However, with wet films as described herein, the weight is not set, due to potential movement of components and volatilization of solvents during drying steps. Thus, maintaining a sufficiently high ratio of solid particles to liquid materials is preferable in keeping a uniform slurry or mixture. Preferably, the film will have a ratio of solid to liquid materials of from about 99 to 1 to about 75 to 25. Most preferably, the film will have a ratio of solid to liquid materials of at least 98 to 2.

Film-Forming Polymers

The polymer may be water soluble, water swellable, water insoluble, or a combination of one or more either water soluble, water swellable or water insoluble polymers. The polymer may include cellulose or a cellulose derivative. Specific examples of useful water soluble polymers include, but are not limited to, pullulan, hydroxypropylmethyl cellulose, hydroxyethyl cellulose, hydroxypropyl cellulose, polyvinyl pyrrolidone, carboxymethyl cellulose, polyvinyl alcohol, sodium aginate, polyethylene oxide, polyethylene glycol, xanthan gum, tragacanth gum, guar gum, acacia gum, arabic gum, polyacrylic acid, methylmethacrylate copolymer, carboxyvinyl copolymers, starch, gelatin, methylcellulose, hypromellose, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

As used herein the phrase "water soluble polymer" and variants thereof refer to a polymer that is at least partially soluble in water, and desirably fully or predominantly soluble in water, or absorbs water. Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a 25 or greater percent by weight water uptake are also useful. Films or dosage forms of the present invention formed from such water soluble polymers are desirably sufficiently water soluble to be dissolvable upon contact with bodily fluids.

Other polymers useful for incorporation into the films of the present invention include biodegradable polymers, copolymers, block polymers and combinations thereof. Among the known useful polymers or polymer classes which meet the above criteria are: poly(glycolic acid) (PGA), poly(lactic acid) (PLA), polydioxanoes, polyoxalates, poly(α-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy)propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of α-amino acids, copolymers of α-amino acids and caproic acid, copolymers of α-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°-347° F. (170°-175° C.); lactide/glycolide 100 L, believed to be 100% glycolide having a melting point within the range of 437°-455° F. (225°-235° C.); lactide/glycolide 85/15, believed to be 85% lactide and 15% glycolide with a melting point within the range of 338°-347° F. (170°-175° C.); and lactide/glycolide 50/50, believed to be a copolymer of 50% lactide and 50% glycolide with a melting point within the range of 338°-347° F. (170°-175° C.).

The Biodel materials represent a family of various polyanhydrides which differ chemically.

Although a variety of different polymers may be used, it is desired to select polymers to provide a desired viscosity of the mixture prior to drying. For example, if the active or other components are not soluble in the selected solvent, a polymer that will provide a greater viscosity is desired to assist in maintaining uniformity. On the other hand, if the components are soluble in the solvent, a polymer that provides a lower viscosity may be preferred.

The polymer plays an important role in affecting the viscosity of the film. Viscosity is one property of a liquid that controls the stability of the active in an emulsion, a colloid or a suspension. Generally the viscosity of the matrix will vary from about 400 cps to about 100,000 cps, preferably from about 800 cps to about 60,000 cps, and most preferably from about 1,000 cps to about 40,000 cps. Desirably, the viscosity of the film-forming matrix will rapidly increase upon initiation of the drying process.

The viscosity may be adjusted based on the selected active depending on the other components within the matrix. For example, if the component is not soluble within the selected solvent, a proper viscosity may be selected to prevent the component from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

It has also been observed that certain polymers which when used alone would ordinarily require a plasticizer to achieve a flexible film, can be combined without a plasticizer and yet achieve flexible films. For example, HPMC and HPC when used in combination, and particularly in combination with polyethylene oxide, provide a flexible, strong film with the appropriate plasticity and elasticity for manufacturing and storage. No additional plasticizer or polyalcohol is needed for flexibility.

Controlled Release Films

The term "controlled release" is intended to mean the release of active at a pre-selected or desired rate. This rate will vary depending upon the application. Desirable rates include fast or immediate release profiles as well as delayed, sustained or sequential release. Combinations of release patterns, such as initial spiked release followed by lower levels of sustained release of active are contemplated. Pulsed drug releases are also contemplated.

The polymers that are chosen for the films of the present invention may also be chosen to allow for controlled disintegration of the active. This may be achieved by providing a substantially water insoluble film that incorporates an active that will be released from the film over time. This may be accomplished by incorporating a variety of different soluble or insoluble polymers and may also include biodegradable polymers in combination. Alternatively, coated controlled release active particles may be incorporated into a readily soluble film matrix to achieve the controlled release property of the active inside the digestive system upon consumption.

Films that provide a controlled release of the active are particularly useful for buccal, gingival, sublingual and vaginal applications. The films of the present invention are particularly useful where mucosal membranes or mucosal fluid is present due to their ability to readily wet and adhere to these areas.

The convenience of administering a single dose of a medication which releases active components in a controlled fashion over an extended period of time as opposed to the administration of a number of single doses at regular intervals has long been recognized in the pharmaceutical arts. The advantage to the patient and clinician in having consistent and uniform blood levels of medication over an extended period of time are likewise recognized. The advantages of a variety of sustained release dosage forms are well known. However, the preparation of a film that provides the controlled release of an active has advantages in addition to those well-known for controlled release tablets. For example, thin films are difficult to inadvertently aspirate and provide an increased patient compliance because they need not be swallowed like a tablet. Moreover, certain embodiments of the inventive films are designed to adhere to the buccal cavity and tongue, where they controllably dissolve. Furthermore, thin films may not be crushed in the manner of controlled release tablets which is a problem leading to abuse of drugs such as Oxycontin.

The actives employed in the present invention may be incorporated into the film compositions of the present invention in a controlled release form. For example, particles of drug may be coated with polymers such as ethyl cellulose or polymethacrylate, commercially available under brand names such as Aquacoat ECD and Eudragit E-100, respectively. Solutions of drug may also be absorbed on such polymer materials and incorporated into the inventive film compositions. Other components such as fats and waxes, as well as sweeteners and/or flavors may also be employed in such controlled release compositions. The actives may be taste-masked prior to incorporation into the film composition.

Actives

When an active is introduced to the film, the amount of active per unit area is determined by the uniform distribution of the film. For example, when the films are cut into individual dosage forms, the amount of the active in the dosage form can be known with a great deal of accuracy. This is achieved because the amount of the active in a given area is substantially identical to the amount of active in an area of the same dimensions in another part of the film. The accuracy in dosage is particularly advantageous when the active is a medicament, i.e. a drug.

Typically, active components are water-active, which refers to those components that may react in the presence or in continued exposure to water-based materials. Such reactions may include, for example, the component crystallizing or becoming amorphous.

The active components that may be incorporated into the films of the present invention include, without limitation pharmaceutical and cosmetic actives, drugs, medicaments, antigens or allergens such as ragweed pollen, spores, microorganisms, seeds, mouthwash components, flavors, fragrances, enzymes, preservatives, sweetening agents, colorants, spices, vitamins and combinations thereof.

A wide variety of medicaments, bioactive active substances and pharmaceutical compositions may be included in the dosage forms of the present invention. Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of medicating active components contemplated for use in the present invention include antacids, $H_2$-antagonists, and analgesics. For example, antacid dosages can be prepared using the components calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (available as Oxycontin®), ibuprofen, aspirin, acetaminophen, and combinations thereof that may optionally include caffeine.

Other preferred drugs for other preferred active components for use in the present invention include anti-diarrheals such as immodium AD, anti-histamines, anti-tussives, decongestants, vitamins, and breath fresheners. Common drugs used alone or in combination for colds, pain, fever, cough, congestion, runny nose and allergies, such as acetaminophen, chlorpheniramine maleate, dextromethorphan, pseudoephedrine HCl and diphenhydramine may be included in the film compositions of the present invention.

Also contemplated for use herein are anxiolytics such as alprazolam (available as Xanax®); anti-psychotics such as clozopin (available as Clozaril®) and haloperidol (available as Haldol®); non-steroidal anti-inflammatories (NSAID's) such as dicyclofenacs (available as Voltaren®) and etodolac (available as Lodine®), anti-histamines such as loratadine (available as Claritin®), astemizole (available as Hismanal™), nabumetone (available as Relafen®), and Clemastine (available as Tavist®); anti-emetics such as granisetron hydrochloride (available as Kytril®) and nabilone (available as Cesamet™); bronchodilators such as Bentolin®, albuterol sulfate (available as Proventil®); anti-depressants such as fluoxetine hydrochloride (available as Prozac®), sertraline hydrochloride (available as Zoloft®), and paroxtine hydrochloride (available as Paxil®); anti-migraines such as Imigra®, ACE-inhibitors such as enalaprilat (available as Vasotec®), captopril (available as Capoten®) and lisinopril (available as Zestril®); anti-Alzheimer's agents, such as nicergoline; and $Ca^H$-antagonists such as nifedipine (available as Procardia® and Adalat®), and verapamil hydrochloride (available as Calan®).

Erectile dysfunction therapies include, but are not limited to, drugs for facilitating blood flow to the penis, and for effecting autonomic nervous activities, such as increasing parasympathetic (cholinergic) and decreasing sympathetic (adrenersic) activities. Useful non-limiting drugs include sildenafils, such as Viagra®, tadalafils, such as Clalis®, vardenafils, apomorphines, such as Uprima®, yohimbine hydrochlorides such as Aphrodyne®, and alprostadils such as Caverject®.

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid components include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

The films made of the present invention are particularly suitable for actives that are highly water sensitive. Non-limiting examples of such water sensitive actives that may be of particular use in this invention include betamethasone valerate, clobetasal propionate, Betamethasone Dipropionate, Flucinolone Acetonide, Hydrocortisone Butyrate, Acyclovir, Mupirocin, Diclofenac, Na Valproate, Ayurvedic, Amitriyptyline HCl, Amoxycillin, Clavulanic Acid, Atorvastatin Cal, Copidogrel, Ethambutol, Glucosamine+, Chondritin, Ranitidine HCl, Famotidine, Cimetidine, Rifampicin, Crixivan, and Aspirin. Other water sensitive compounds may be incorporated into the films of the present invention.

An anti-oxidant may also be added to the film to prevent the degradation of an active, especially where the active is photosensitive.

Cosmetic active agents may include breath freshening compounds like menthol, other flavors or fragrances, especially those used for oral hygiene, as well as actives used in dental and oral cleansing such as quaternary ammonium bases. The effect of flavors may be enhanced using flavor enhancers like tartaric acid, citric acid, vanillin, or the like.

Also color additives can be used in preparing the films. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cinnamon, cocoa, and citrus oils such as lemon, orange, grape, lime and grapefruit and fruit essences including apple, pear, peach, grape, strawberry, raspberry, cherry, plum, pineapple, apricot or other fruit flavors.

The films containing flavorings may be added to provide a hot or cold flavored drink or soup. These flavorings include, without limitation, tea and soup flavorings such as beef and chicken.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The sweeteners may be chosen from the following non-limiting list: glucose (corn syrup), dextrose, invert sugar, fructose, and combinations thereof; saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; isomalt; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof, and natural intensive sweeteners, such as Lo Han Kuo. Other sweeteners may also be used.

When the active is combined with the polymer in the solvent, the type of matrix that is formed depends on the solubilities of the active and the polymer. If the active and/or polymer are soluble in the selected solvent, this may form a solution. However, if the components are not soluble, the matrix may be classified as an emulsion, a colloid, or a suspension.

Dosages

The film products of the present invention are capable of accommodating a wide range of amounts of the active component. The films are capable of providing an accurate dosage amount (determined by the size of the film and concentration of the active in the original polymer/water combination) regardless of whether the required dosage is high or extremely low. Therefore, depending on the type of active or pharmaceutical composition that is incorporated into the film, the active amount may be as high as about 300 mg, desirably up to about 150 mg or as low as the microgram range, or any amount therebetween.

The film products and methods of the present invention are well suited for high potency, low dosage drugs. This is accomplished through the high degree of uniformity of the films. Therefore, low dosage drugs, particularly more potent racemic mixtures of actives are desirable.

Anti-Foaming and De-Foaming Compositions

Anti-foaming and/or de-foaming components may also be used with the films of the present invention. These components aid in the removal of air, such as entrapped air, from the film-forming compositions. As described above, such entrapped air may lead to non-uniform films. Simethicone is one particularly useful anti-foaming and/or de-foaming agent. The present invention, however, is not so limited and other anti-foam and/or de-foaming agents may suitable be used.

Simethicone is generally used in the medical field as a treatment for gas or colic in babies. Simethicone is a mixture of fully methylated linear siloxane polymers containing repeating units of polydimethylsiloxane which is stabilized with trimethylsiloxy end-blocking unites, and silicon dioxide. It usually contains 90.5-99% polymethylsiloxane and 4-7% silicon dioxide. The mixture is a gray, translucent, viscous fluid which is insoluble in water.

When dispersed in water, simethicone will spread across the surface, forming a thin film of low surface tension. In this way, simethicone reduces the surface tension of bubbles air located in the solution, such as foam bubbles, causing their collapse. The function of simethicone mimics the dual action of oil and alcohol in water. For example, in an oily solution any trapped air bubbles will ascend to the surface and dissipate more quickly and easily, because an oily liquid has a lighter density compared to a water solution. On the other hand, an alcohol/water mixture is known to lower water density as well as lower the water's surface tension. So, any air bubbles trapped inside this mixture solution will also be easily dissipated. Simethicone solution provides both of these advantages. It lowers the surface energy of any air bubbles that trapped inside the aqueous solution, as well as lowering the surface tension of the aqueous solution. As the result of this unique functionality, simethicone has an excellent anti-foaming property that can be used for physiological processes (anti-gas in stomach) as well as any for external processes that require the removal of air bubbles from a product.

In order to prevent the formation of air bubbles in the films of the present invention, the mixing step can be performed under vacuum. However, as soon as the mixing step is completed, and the film solution is returned to the normal atmosphere condition, air will be re-introduced into or contacted with the mixture. In many cases, tiny air bubbles will be again trapped inside this polymeric viscous solution. The incorporation of simethicone into the film-forming composition either substantially reduces or eliminates the formation of air bubbles.

Simethicone may be added to the film-forming mixture as an anti-foaming agent in an amount from about 0.01 weight percent to about 5.0 weight percent, more desirably from about 0.05 weight percent to about 2.5 weight percent, and most desirably from about 0.1 weight percent to about 1.0 weight percent.

Optional Components

A variety of other components and fillers may also be added to the films of the present invention. These may include, without limitation, surfactants; plasticizers which assist in compatibilizing the components within the mixture; polyalcohols; anti-foaming agents, such as silicone-containing compounds, which promote a smoother film surface by releasing oxygen from the film; and thermo-setting gels such as pectin, carageenan, and gelatin, which help in maintaining the dispersion of components.

The variety of additives that can be incorporated into the inventive compositions may provide a variety of different functions. Examples of classes of additives include excipients, lubricants, buffering agents, stabilizers, blowing agents, pigments, coloring agents, fillers, bulking agents, sweetening agents, flavoring agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active component(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragacanth), pectin, water-soluble derivatives of cellulose: alkylcelluloses hydroxyalkylcelluloses and hydroxyalkylalkylcelluloses, such as methylcelluose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water soluble chemical derivatives of starch, cationically modified acrylates and methacrylates possessing, for example, a tertiary or quaternary amino group, such as the diethylaminoethyl group, which may be quaternized if desired; and other similar polymers.

Such extenders may optionally be added in any desired amount desirably within the range of up to about 80%, desirably about 3% to 50% and more desirably within the range of 3% to 20% based on the weight of all components.

Further additives may be inorganic fillers, such as the oxides of magnesium aluminum, silicon, titanium, etc. desirably in a concentration range of about 0.02% to about 3% by weight and desirably about 0.02% to about 1% based on the weight of all components.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer.

There may further be added compounds to improve the flow properties of the starch material such as animal or vegetable fats, desirably in their hydrogenated form, especially those which are solid at room temperature. These fats desirably have a melting point of 50° C. or higher. Preferred are tri-glycerides with $C_{12}$-, $C_{14}$-, $C_{16}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{18}$-, $C_{20}$- and $C_{22}$-fatty acids.

The total amounts used of the fats, mono-, di-glycerides and/or lecithins are up to about 5% and preferably within the range of about 0.5% to about 2% by weight of the total composition It is further useful to add silicon dioxide, calcium silicate, or titanium dioxide in a concentration of about 0.02% to about 1% by weight of the total composition. These compounds act as texturizing agents.

These additives are to be used in amounts sufficient to achieve their intended purpose. Generally, the combination of certain of these additives will alter the overall release profile of the active component and can be used to modify, i.e. impede or accelerate the release.

Lecithin is one surface active agent for use in the present invention. Lecithin can be included in the feedstock in an amount of from about 0.25% to about 2.00% by weight. Other surface active agents, i.e. surfactants, include, but are not limited to, cetyl alcohol, sodium lauryl sulfate, the Spans™ and Tweens™ which are commercially available from ICI Americas, Inc. Ethoxylated oils, including ethoxylated castor oils, such as Cremophor® EL which is commercially available from BASF, are also useful. Carbowax™ is yet another modifier which is very useful in the present invention. Tweens™ or combinations of surface active agents may be used to achieve the desired hydrophilic-lipophilic balance ("HLB"). The present invention, however, does not require the use of a surfactant and films or film-forming compositions of the present invention may be essentially free of a surfactant while still providing the desirable uniformity features of the present invention.

As additional modifiers which enhance the procedure and product of the present invention are identified, Applicants intend to include all such additional modifiers within the scope of the invention claimed herein.

Other components include binders which contribute to the ease of formation and general quality of the films. Non-limiting examples of binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

Forming the Film

Although the films of the present invention preferably are described herein according to certain parameters, it will be understood that these may be altered in various ways without substantially affecting the resulting end product.

The matrix, including the film-forming polymer and solvent, in addition to any additives and the active component, may be formed in a number of steps. In one embodiment of the invention, the components may be added together in separate pre-mixed batches. The advantage of a pre-mix is that all components except for the active or any other water-active components may be combined in advance. The water-active components, such as certain actives, taste-masking components, or other components that may react with the solvent, may be added to the solvent matrix just prior to formation of the film. This is especially important for components that may degrade with prolonged exposure to water, air or another polar solvent.

In this particular method of forming the matrix, the pre-mix, which includes the water-based materials, such as the film-forming polymer and solvent, and any other additives that are not water-active may be mixed in one container. The solvent may be any desired solvent, and may be an organic solvent, a non-polar solvent, a polar solvent, and combinations thereof. Further, the solvent may have a high pH, a low pH or a neutral pH. In addition, the solvent may have a low or no salt concentration, or alternatively it may have a high salt concentration. The resulting mixture is referred to as the "water-based solution". Concurrently, in a separate container, a second pre-mix is prepared, which includes the pharmaceutically active agent, as well as any other water-active components desired, including, for example, taste-masking components. In this second pre-mix, called the "water-actives mixture" or "water-active slurry", there may be little to no water-based materials. The water-actives mixture may be in any desired form, and may be in the form of a slurry, an emulsion, a solution, a suspension, a colloid dispersion, or combinations thereof. This dual mix embodiment limits the contact between the water-active components and the water-based materials, effectively reducing or eliminating reaction between the two components. Components that do not react with the water-based materials may be added to either pre-mix, or may be added separately.

After the two pre-mixed materials have been prepared, they can then be mixed and dispensed using a rapid mixing system. The components may be combined and dispensed using a so-called "meter-mix-dispense" system, described herein. In this embodiment, the two separate pre-mixes are added into the mixing compartment in pre-determined amounts at or about the same time, or metered through the inline mixer at substantially constant and predetermined rates. When in the mixer, the pre-mixes are blended with a very high shear mixer, which allows them to be sufficiently combined in a very short time. In one embodiment, the residence time for mixed components may be on the order of seconds, including as low as about 1 second. In other embodiments, the residence time in the inline mixer may be several minutes, including about 5-10 minutes. After this rapid but effective mixing stage, the mixed solution is then dispensed rapidly from the mixer. Other embodiments include adding various components separately directly to the mixer, having more than two pre-mixed batches, and any other means to add while keeping the water-active and water-based components separate until mixing.

Various types of mixing systems are contemplated herein, including, but not limited to static mixers, dynamic mixers, and small and large volume inline mixers. The compositions may optionally be combined and mixed continuously in any desired mixer. Mixers may allow for continuous flow of components or the components may be intermittent, or there may be a combination, wherein particular components are continuously fed into the mixer, while others may be fed intermittently. The system may incorporate intermittent charging of a mix head, which may be accomplished, for example, with piston pumps, prior to or concurrently with the mixing and dispensing steps. In one embodiment, the compositions may be combined and mixed using a small volume inline mixer, which may be intermittently charged with aliquots of solution and slurry, metered, and then discharged.

Any means to form the film may be used, including extrusion, coating, casting and the like. The film may be formed directly from the dispensing device, or it may enter a separate dispensing means where it may then be coated or casted into a film. Alternatively, the components may be dispensed into a reservoir or trough, where the film is formed by coating the mixed components onto a substrate. Once the film is formed, i.e., by coating, casting, extruding, or the like, the film may then be rapidly dried, allowing the water-based portions of the solution to be evaporated and thus removed quickly. Any means of drying may be used, including those described herein. Rapid drying and removal of the water-based materials helps to reduce and limit the amount of time that the water-active components are in contact with water-based materials. As described above, this further limits and reduces the tendency of the water-active components to react with the water.

Preferably, the water-active components are exposed to water-based materials for about 1 second to about 10 minutes, and more preferably are exposed for no longer than under about 1 second to about 5 minutes. In addition to the limited time exposure, other variables may help reduce the tendency of the water-active components to react with the water-based solution, including, but not limited to mixing speed, temperature, drug percentage, stream flow ratios and slurry ratios. The mixing speed is preferably from zero (as in the case of static mixers) to about 10,000 rpm for very high intensity mixers. The temperature for mixing is preferably from 4° C. to 80° C.

In addition, the stream ratio, i.e., the ratio of solids to liquids, is optimally 1:1000 to 1:1. The flow stream is preferably a speed of about 50 g/min to about 500 g/min. Further, the optimal slurry ratio is about 20% solids to about 80% solids.

In some embodiments it may be preferred to use a coated drug slurry, which may then be metered into a flow stream of coating solution. In this embodiment, the desired active agent is first coated with a desired coating. Coatings may be desired since the active agent may be water sensitive, and the coating would thus protect the active from substantial contact with a water-based stream. Suitable coatings include moisture barrier polymers such as Eudragit L30 D-55, Eudragit E100, Opadry AMP (a polyvinylacetate), Sepifilm LB 014 (HPMC/MCC and Stearic Acid), Aquacoat CPD, Aquacoat ECD, and CAP (cellulose acetate phthalate). In a preferred embodiment, CAP is used as the coating. For example, one may coat an active agent with CAP plus a plasticizer, and then disperse the coated particle in ethanol as a co-solvent. The coated drug/ethanol slurry may then be metered into a flow stream of coating solution at any desired stream ratio.

Using a rapid mix and dispense system as described herein further allows for a continuous addition of the various components, including, in one embodiment, the pre-mixed slurry and pre-mixed water-based solution into the mixer, substantially reducing the amount of cleaning and sanitizing of the mixer between batches of films, as would normally be required in traditional systems.

In some embodiments, it may be desirable to include a system for monitoring of the concentration of the various components in the film, either while in the mixer, after extrusion, after drying, or any other stage in the film-forming process. For example, it may be desirable to monitor the active pharmaceutical ingredient (API) concentration in the film, such as to comply with various regulatory and other governmental requirements. Any means for monitoring the various levels of concentration in the film composition may be used, such as by using known spectroscopy or other analytical mechanisms. One such preferred method of monitoring the concentration of the API in the process of manufacturing film described herein is by use of Fourier Transform Near-Infrared Spectroscopy (FT-NIR). Particularly useful monitoring may be accomplished by use of a multi-probe continuous FT-NIR system, which monitors the concentration of APIs throughout the span of the film web during manufacture.

In some embodiments, it may be desirable to use one or more additives to inhibit the solubility of a taste-masked coating during the formation and mixing process. During the drying process, the additive may be removed through the application of heat and/or radiation energy. For example, $CO_2$ may be used as carbonic acid to inhibit the solubility of the taste masking coating. During the formation process, the $CO_2$ may be removed through the application of energy.

If a multi-layered film is desired, this may be accomplished by coating, spreading, or casting a combination onto an already formed film layer. Alternatively, the layers may be co-extruded together. Although a variety of different film-forming techniques may be used, it may be desirable to select a method that will provide a flexible film, such as reverse roll coating. The flexibility of the film allows for the sheets of film to be rolled and transported for storage or prior to being cut into individual dosage forms. Desirably, the films will also be self-supporting or in other words able to maintain their integrity and structure in the absence of a separate support. Furthermore, the films of the present invention may be selected of materials that are edible or ingestible.

Coating or casting methods are particularly useful for the purpose of forming the films of the present invention. Specific examples include reverse roll coating or casting, gravure coating, immersion or dip coating, metering rod or meyer bar coating, slot die or extrusion coating, gap or knife over roll coating, air knife coating, curtain coating, or combinations thereof, especially when a multi-layered film is desired.

Roll coating, or more specifically reverse roll coating, is particularly desired when forming films in accordance with the present invention. This procedure provides excellent control and uniformity of the resulting films, which is desired in the present invention. In this procedure, the coating material is measured onto the applicator roller by the precision setting of the gap between the upper metering roller and the application roller below it. The coating is transferred from the application roller to the substrate as it passes around the support roller adjacent to the application roller. Multiple roll processes, such as three roll and four roll processes, are commonly known in the art.

The gravure coating process relies on an engraved roller running in a coating bath, which fills the engraved dots or lines of the roller with the coating material. The excess coating on the roller is wiped off by a doctor blade and the coating is then deposited onto the substrate as it passes between the engraved roller and a pressure roller.

Offset Gravure is common, where the coating is deposited on an intermediate roller before transfer to the substrate.

In the process of immersion or dip coating, the substrate is dipped into a bath of the coating, which is normally of a low viscosity to enable the coating to run back into the bath as the substrate emerges.

In the metering rod coating process, an excess of the coating is deposited onto the substrate as it passes over the bath roller. The wire-wound metering rod, sometimes known as a Meyer Bar, allows the desired quantity of the coating to remain on the substrate. The quantity is determined by the diameter of the wire used on the rod.

In the slot die process, the coating is squeezed out by gravity or under pressure through a slot and onto the substrate. If the coating is about 100% solids, the process is termed "extrusion" and in this case, the line speed is frequently much faster than the speed of the extrusion. This enables coatings to be considerably thinner than the width of the slot.

The gap or knife over roll process relies on a coating being applied to the substrate which then passes through a "gap" between a "knife" and a support roller. As the coating and substrate pass through, the excess is scraped off.

Air knife coating is where the coating is applied to the substrate and the excess is "blown off" by a powerful jet from the air knife. This procedure is useful for aqueous coatings.

In the curtain coating process, a bath with a slot in the base allows a continuous curtain of the coating to fall into the gap between two conveyors. The object to be coated is passed along the conveyor at a controlled speed and so receives the coating on its upper face.

Drying the Film

A controlled drying process may be used to dry the film, and may additionally reduce the variability of the composition in the film. As explained above, the manufacturing method described herein preferably incorporates rapid drying in order to more quickly remove the water-based materials, and reduce the time that the water-active components are in contact therewith. Rapid removal of solvent allows the film to form a visco-elastic mass in about 0.5 to about 10 minutes, which locks in the uniformity of content in the film. Drying methods used herein are preferred so as to ensure that there is a substantially uniform content of materials in the film. Controlled drying methods are useful in eliminating the formation of bubbles in the film as it is drying, thereby reducing the likelihood of variability of content in the film. An alternative method of forming a film with an accurate dosage, that would not necessitate the controlled drying process, would be to cast the films on a predetermined well. With this method, although the components may aggregate, this will not result in the migration of the active to an adjacent dosage form, since each well may define the dosage unit per se. When a controlled or rapid drying process is desired, such controlled drying may be achieved through a variety of methods. A variety of methods may be used including those that require the application of heat energy and/or radiation energy, such as heat, microwaves, infrared or other similar energy. The liquid carriers are removed from the film in a manner such that the uniformity, or more specifically, the non-self-aggregating uniform heterogeneity, that is obtained in the wet film is maintained.

Desirably, the film is dried from the bottom of the film to the top of the film. More desirably, substantially no air flow is present across the top of the film during its initial setting period, during which a solid, visco-elastic structure is formed. This can take place within the first few minutes, e.g. about the first 0.5 to about 10.0 minutes of the drying process, and more desirably within the first about 0.5 to about 4.0 minutes of the drying process. Controlling the drying in this manner prevents the destruction and reformation of the film's top surface. This is accomplished by forming the film and placing it on the top side of a surface having top and bottom sides. Then, heat is initially applied to the bottom side of the film to provide the necessary energy to evaporate or otherwise remove the liquid carrier. The films dried in this manner dry more quickly and evenly as compared to air-dried films, or those dried by conventional drying means. In contrast to an air-dried film that dries first at the top and edges, the films dried by applying heat to the bottom dry simultaneously at the center as well as at the edges. This also prevents settling of components that occurs with films dried by conventional means. Suitable drying methods include those described in U.S. Pat. Nos. 7,357,891 and 7,425,292, the entire contents of which are incorporated herein by reference.

The temperature of the matrix during the drying step is about 100° C. or less, desirably about 90° C. or less, and most desirably about 80° C. or less. The temperature surrounding the matrix may be higher if desired, but desirably the temperature of the drying matrix is maintained at a temperature below about 100° C., or the degradation temperature of any active present within the matrix, whichever is greater.

Another method of controlling the drying process, which may be used alone or in combination with other controlled methods as disclosed above includes controlling and modifying the humidity within the drying apparatus where the film is being dried. In this manner, the premature drying of the top surface of the film is avoided.

Additionally, the length of drying time can be properly controlled, i.e. balanced, with the heat sensitivity and volatility of the components, and particularly the flavor oils and drugs. The amount of energy, temperature and length and speed of the conveyor can be balanced to accommodate such actives and to minimize loss, degradation or ineffectiveness in the final film.

The films may initially have a thickness of about 500 μm to about 1,500 μm, or about 20 mils to about 60 mils, which may be controlled by varying the gap between the doctor roll and drive roll, and when dried have a thickness in the desired range set forth above.

Uses of Thin Films

The thin films of the present invention are well suited for many uses. The high degree of uniformity of the components of the film makes them particularly well suited for incorporating pharmaceuticals. Furthermore, the polymers used in construction of the films may be chosen to allow for a range of disintegration times for the films. A variation or extension in the time over which a film will disintegrate may achieve control over the rate that the active is released, which may allow for a sustained release delivery system. In addition, the films may be used for the administration of an active to any of several body surfaces, especially those including mucous membranes, such as oral, anal, vaginal, opthalmological, the surface of a wound, either on a skin surface or within a body such as during surgery, and similar surfaces. Buccal and sublingual administration routes may be particularly useful.

The films may be used to orally administer an active. This is accomplished by preparing the films as described above and introducing them to the oral cavity of a mammal. This film may be prepared and adhered to a second or support layer from which it is removed prior to use, i.e. introduction to the oral cavity. An adhesive may be used to attach the film to the support or backing material which may be any of those known in the art, and is preferably not water soluble. If an adhesive is used, it will desirably be a food grade adhesive that is ingestible and does not alter the properties of the active. Mucoadhesive compositions are particularly useful. The film compositions in many cases serve as mucoadhesives themselves.

The films may be applied under or to the tongue of the mammal. When this is desired, a specific film shape, corresponding to the shape of the tongue may be preferred. Therefore the film may be cut to a shape where the side of the film corresponding to the back of the tongue will be longer than the side corresponding to the front of the tongue. Specifically, the desired shape may be that of a triangle or trapezoid. Desirably, the film will adhere to the oral cavity preventing it from being ejected from the oral cavity and permitting more of the active to be introduced to the oral cavity as the film dissolves.

Another use for the films of the present invention takes advantage of the films' tendency to dissolve quickly when introduce to a liquid. An active may be introduced to a liquid by preparing a film in accordance with the present invention, introducing it to a liquid, and allowing it to dissolve. This may be used either to prepare a liquid dosage form of an active, or to flavor a beverage.

The films of the present invention are desirably packaged in sealed, air and moisture resistant packages to protect the active from exposure oxidation, hydrolysis, volatilization and interaction with the environment. Additionally, they can include a dispenser, which may contain a full supply of the medication typically prescribed for the intended therapy, but due to the thinness of the film and package, is smaller and more convenient than traditional bottles used for tablets, capsules and liquids. Moreover, the films of the present invention dissolve quickly upon contact with saliva or mucosal membrane areas, eliminating the need to wash the dose down with water.

Desirably, a series of such unit doses are packaged together in accordance with the prescribed regimen or treatment, e.g., a 10-90 day supply, depending on the particular therapy. The individual films can be packaged on a backing and peeled off for use.

The features and advantages of the present invention are more fully shown by the following examples which are provided for purposes of illustration, and are not to be construed as limiting the invention in any way.

EXAMPLES

Example 1

Formation of Film

Prednisolone sodium phosphate is coated with a 40% by weight coating of Eudragit® L 100-55. The coated particles are suspended in an aqueous slurry of carbonic acid with a pH of 5.0 and stored in a $CO_2$ atmosphere of 0.01 atmospheres. Separately, a polymer solution is made, which includes polyethylene oxide, methylcellulose, flavors, sweeteners and other excipients. The solution and the slurry are pumped using metering pumps through a mixer, where they are mixed for a short period of time, and then sent into a slot die coater and onto a substrate. The result is a wet film coated onto the substrate. The wet film is then dried in an drying oven. The $CO_2$ is lost in the drying oven, which results in a raised pH of the film. The resultant film thus includes the desired level of active and includes a soluble taste-masked coating. The film may then be ingested by an individual.

Example 2

Formation of Film

Prednisolone sodium phosphate is coated with a 40% by weight coating of Methocel 310. The coated particles are suspended in a solution of isopropanol. Separately, a polymer solution is made including PEO, methylcellulose, flavors, sweeteners and other excipients. The suspension and the polymer solution are then pumped using metering pumps through a static mixer, where the suspension and the polymer solution are mixed for a short period of time. The resultant mixture is then fed into a slot die coater and onto a substrate. The result is a wet film coated onto the substrate. The wet film is then dried in a drying oven to effectively remove the isopropanol and produce a self-supporting film product.

Example 3

Dissolution of Actives

Actives may dissolve at different rates depending on the pH of the solution into which the actives are placed. The dissolved actives, once leached from a taste masking medium, will impart a bad taste to the film. As a result, it is desirable to keep the time spend in a lower pH solution at a minimum.

Figure 1:
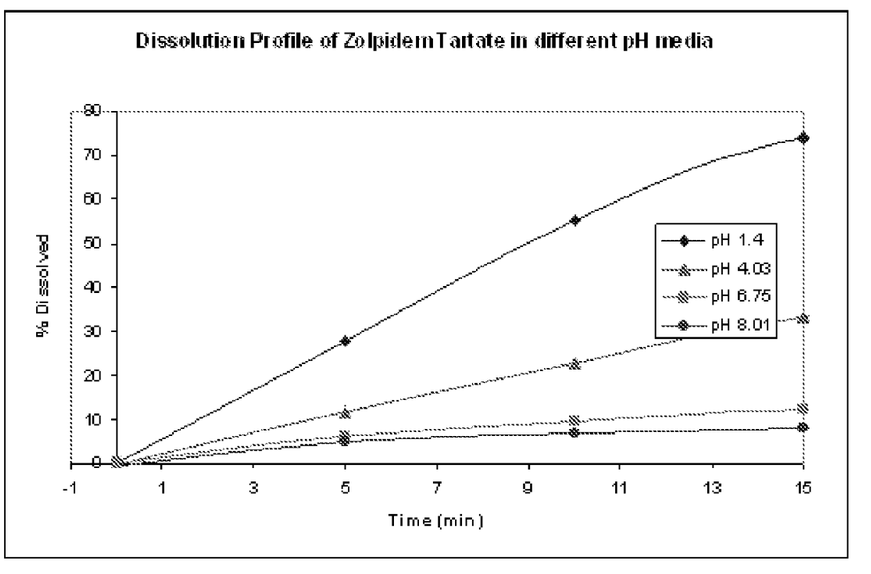
FIG. 1 is a graphic depiction of the dissolution profile of one active in various pH media.

One active, Zolpidem Tart, was coated with a 40% by weight coating of Eudragit® L 100-55, and placed into various media having pH levels from about 1 to about 8, and the dissolution rate of the active for each solution was measured. The results are set forth in FIG. 1. As can be seen, the lower the pH of the solution, the quicker the dissolution of the active. Further, even in neutral solutions, the active dissolves over a period of time. Thus, it is desirable to limit the time that the active is exposed to a solution, especially that having a low pH value. It would therefore be preferable to mix the taste-masked active in a high or neutral pH solution separately, and then mix with a low pH polymer solution. This effectively limits the exposure of the taste-masked active to the low pH solution.

What is claimed is:

1. A process for making an edible film having a substantially uniform distribution of components, comprising the steps of: a. combining a water-based film polymer solution and a slurry mixture, wherein said slurry mixture comprises a water-active component and a solvent, said slurry mixture having no water-based materials added; b. mixing the polymer solution and slurry mixture for about 10 minutes or less; c. dispensing the mixed solution and slurry mixture to form a film; and d. rapidly removing said solvent from said film.

2. The process of claim 1, wherein said water-active component is a pharmaceutically active agent.

3. The process of claim 1, wherein said water-active component is a taste masking agent.

4. The process of claim 1, wherein said steps of combining and mixing are performed using a meter-mix-dispense system.

5. The process of claim 1, wherein said steps of combining and mixing are performed using a continuous metered flow through a static mixer.

6. The process of claim 1, wherein said steps of combining and mixing are performed using a continuous metered flow through a dynamic mixer.

7. The process of claim 1, wherein said steps of combining and mixing are performed using a small volume inline mixer, charged with aliquots of solution and slurry mixture, mixed and discharged.

8. The process of claim 1, wherein said polymer solution and slurry mixture are mixed for 60 seconds or less.

9. The process of claim 1, wherein said step of rapidly removing said solvent results in the film forming a viscoelastic structure.

10. The process of claim 1, wherein said mixed polymer solution and slurry mixture are extruded to form said film.

11. The process of claim 1, wherein said mixed polymer solution and slurry mixture are cast into a film.

12. The process of claim 1, wherein said mixed polymer solution and slurry mixture are dispensed into a reservoir.

13. The process of claim 12, wherein said mixed polymer solution and slurry mixture are coated onto a substrate.

14. The process of claim 1, wherein said edible film comprises a polymer and an active, wherein said active is at least partially coated with a water-soluble or partially water-soluble coating and wherein said coating is substantially insoluble in organic solvent.

15. A method for reducing the interaction between a water-active component and water-based film polymer solution during formation of an edible film, comprising the steps of: a. combining a water-based film polymer solution and a slurry mixture, wherein said slurry mixture comprises a water-active component and a solvent, said slurry mixture having no water-based materials added; b. mixing the polymer solution and slurry mixture for about 10 minutes or less; c. dispensing the mixed solution and slurry mixture to form a film; and d. rapidly removing said solvent from said film.

16. The method of claim 15, wherein said water-active component is a pharmaceutically active agent.

17. The method of claim 15, wherein said water-active component is a taste masking agent.

18. The method of claim 15, wherein said steps of adding a water-based film polymer solution into a mixer, simultaneously adding a slurry mixture into said mixer, mixing the polymer solution and slurry mixture for 10 minutes or less, and wherein dispensing said mixed solution and slurry mixture is performed using a meter-mix-dispense system.

19. The method of claim 15, wherein said polymer solution and slurry mixture are mixed for 60 seconds or less.

20. The method of claim 15, wherein said step of rapidly removing said solvent results in the film forming a viscoelastic structure.

21. The method of claim 15, wherein said mixed polymer solution and slurry mixture are extruded to form said film.

22. The method of claim 15, wherein said mixed polymer solution and slurry mixture are cast into a film.

23. The method of claim 15, wherein said mixed polymer solution and slurry mixture are dispensed into a reservoir.

24. The method of claim 23, wherein said mixed polymer solution and slurry mixture are coated onto a substrate.

25. The process of claim 15, wherein said edible film comprises a polymer and an active, wherein said active is at least partially coated with a water-soluble or partially water-soluble coating and wherein said coating is substantially insoluble in organic solvent.

26. A method of substantially limiting interaction of a pharmaceutical agent with a water-based solvent during the formation of an edible film, comprising the steps of: a. simultaneously adding a water-based film polymer solution and a slurry mixture into a mixer, wherein said slurry mixture comprises a pharmaceutical agent and a solvent, said slurry mixture having no water-based materials added; b. mixing said polymer solution and slurry mixture for about 10 minutes or less; c. dispensing the mixed solution and slurry mixture to form a film; and d. rapidly removing said solvent from said film.

27. The method of claim 26, wherein said steps of combining and mixing are performed using a meter-mix-dispense system.

28. The method of claim 26, wherein said polymer solution and slurry mixture are mixed for 60 seconds or less.

29. The method of claim 26, wherein said step of rapidly removing said solvent results in the film forming a viscoelastic structure.

30. The method of claim 26, wherein said mixed polymer solution and slurry mixture are extruded to form said film.

31. The method of claim 26, wherein said mixed polymer solution and slurry mixture are cast into a film.

32. The method of claim 26, wherein said mixed polymer solution and slurry mixture are dispensed into a reservoir.

33. The method of claim 32, wherein said mixed polymer solution and slurry mixture are coated onto a substrate.

34. The process of claim 26, wherein said edible film comprises a polymer and an active, wherein said active is at least partially coated with a water-soluble or partially water-soluble coating and wherein said coating is substantially insoluble in organic solvent.

* * * * *